US011642506B1

(12) United States Patent
Liu et al.

(10) Patent No.: US 11,642,506 B1
(45) Date of Patent: May 9, 2023

(54) MULTI-LAYERED MICRONEEDLE PATCH AND METHOD OF MANUFACTURING THE SAME

(71) Applicant: Win Coat Corporation, Hsinchu (TW)

(72) Inventors: Ta-Jo Liu, Hsinchu (TW); Wan-Hua Li, Hsinchu (TW); Han-Yin Cheng, Hsinchu (TW); Yi-Jyun Liao, Hsinchu (TW); Wen-Hsu Lien, Hsinchu (TW); Shin-Yi Yin, Hsinchu (TW); Ying-Hua Hsu, Hsinchu (TW); Hsiu-Feng Yeh, Hsinchu (TW)

(73) Assignee: Win Coat Corporation, Hsinchu (TW)

( * ) Notice: Subject to any disclaimer, the term of this patent is extended or adjusted under 35 U.S.C. 154(b) by 0 days.

(21) Appl. No.: 17/572,838

(22) Filed: Jan. 11, 2022

(30) Foreign Application Priority Data

Dec. 2, 2021 (TW) .................................. 110144965

(51) Int. Cl.
*A61M 37/00* (2006.01)
*A61L 31/04* (2006.01)
(Continued)

(52) U.S. Cl.
CPC ....... *A61M 37/0015* (2013.01); *A61L 31/041* (2013.01); *B29C 41/003* (2013.01); *B29C 41/22* (2013.01); *A61M 2037/0023* (2013.01); *A61M 2037/0053* (2013.01); *A61M 2202/30* (2013.01); *B29K 2029/04* (2013.01); *B29K 2105/0035* (2013.01); *B29L 2031/7544* (2013.01)

(58) Field of Classification Search
CPC ...... A61M 37/0015; A61M 2037/0023; A61M 2037/0053; A61M 2202/30; A61L 31/041; B29C 41/003; B29C 41/22; B29K 2029/04; B29K 2105/0035; B29L 2031/7544
See application file for complete search history.

(56) References Cited

U.S. PATENT DOCUMENTS

| 2014/0005606 A1 | 1/2014 | Chen et al. |
| 2015/0238434 A1* | 8/2015 | Yoshida ................ B29C 59/005 424/443 |

(Continued)

FOREIGN PATENT DOCUMENTS

| CN | 110870846 A | 3/2020 |
| CN | 110917176 A | 3/2020 |

(Continued)

*Primary Examiner* — Amber R Stiles
(74) *Attorney, Agent, or Firm* — Birch, Stewart, Kolasch & Birch, LLP

(57) ABSTRACT

Provided is a microneedle patch comprising a substrate part and multiple needle parts protruding from the substrate part. The substrate part consists of a diffusion-proof layer and a base, and each needle part consists of a needle tip, a diffusion-proof layer and a base. The diffusion-proof layer of each needle part is formed between the needle tip and the base of the corresponding needle part. The diffusion-proof layer of the substrate part and the diffusion-proof layer of needle part are one-piece structures, and so are the base of the substrate part and the base of the needle part. The diffusion-proof layer of the microneedle patch can prevent the active ingredients from diffusing to the base, limit the active ingredients to the needle tip and control the carrying quantity thereof.

18 Claims, 5 Drawing Sheets

(51) Int. Cl.
  *B29C 41/00* (2006.01)
  *B29C 41/22* (2006.01)
  *B29K 105/00* (2006.01)
  *B29K 29/00* (2006.01)
  *B29L 31/00* (2006.01)

(56) References Cited

U.S. PATENT DOCUMENTS

2018/0243543 A1   8/2018   Baek et al.
2021/0178138 A1   6/2021   Gao et al.

FOREIGN PATENT DOCUMENTS

| CN | 112999297 A | 6/2021 |
| CN | 113288882 A | 8/2021 |
| JP | 2014-18507 A | 2/2014 |
| KR | 13-2818-0080476 A | 7/2018 |
| TW | 202039022 A | 11/2020 |
| TW | 1741732 B | 10/2021 |
| WO | WO 2010/140401 A1 | 12/2010 |
| WO | WO 2017/104144 A1 | 6/2017 |
| WO | WO 2017/179615 A1 | 10/2017 |
| WO | WO 2020/200194 A1 | 10/2020 |

\* cited by examiner

MULTI-LAYERED MICRONEEDLE PATCH AND METHOD OF MANUFACTURING THE SAME

CROSS-REFERENCE TO RELATED APPLICATION

Pursuant to 35 U.S.C. § 119(a), this application claims the benefits of the priority to Taiwan Patent Application No. 110144965, filed Dec. 2, 2021. The contents of the prior application are incorporated herein by its entirety.

BACKGROUND OF THE INVENTION

1. Field of the Invention

The present invention relates to a microneedle patch and a method of manufacturing the same, and more particularly to a microneedle patch applicable to cosmetic, pharmaceutical or vaccine fields, and a method of manufacturing the same.

2. Description of the Prior Arts

Recently, transdermal drug delivery has become a high-profile non-invasive way of drug administration that exerts the effects of active ingredients, such as drugs or vaccines, by skin absorption. Although the transdermal drug delivery can avoid drug degradation caused by the digestive system and primary liver metabolism resulted from oral administration and also can eliminate the fear and pain resulted from subcutaneous injection, the conventional transdermal drug delivery is not suitable for water-soluble drugs or water-soluble vaccines due to the hydrophobic and negatively charged properties of the stratum corneum of skin.

For the aforementioned drawbacks, the prior art has developed a microneedle patch with multiple micron-sized microneedle structures on its substrate. Those microneedle structures can pierce the stratum corneum of the skin, and deliver and release drugs or vaccines to the epidermis. Drug administration with the microneedle patch not only solves many problems caused by oral administration or subcutaneous injection, but also further expands the types of delivered drugs or vaccines to fat-soluble and water-soluble, such that the foresaid different kinds of drugs or vaccines can be directly delivered and released to the epidermis or the dermis by the microneedle structures of the microneedle patch without causing any pain.

Based on the advantages of the microneedle patch, the industry has actively invested in the development of the microneedle patch. For example, Taiwan patent application No. 201400140A discloses a method of manufacturing an embeddable patch for transdermal drug delivery. The method comprises the following steps: mold-filling a biodegradable polymer gel containing drugs to obtain a plurality of biodegradable carriers, manufacturing a supporting substrate having a plurality of protruded supporting shafts and then applying an adhesive on the supporting substrate, and aligning the protruded supporting shafts on the surface of the supporting substrate to the biodegradable carriers to adhere to each other for obtaining the embeddable patch for transdermal drug delivery.

However, the foresaid method needs to give additional consideration about the distance and aligning accuracy between the plurality of protruded supporting shafts on the supporting substrate and the plurality of biodegradable carriers, thereby increasing the difficulty of the preparing processes. Besides, during the preparing process, the step of applying the adhesive is necessary before adhering to the supporting substrate and the biodegradable carriers, which increases the complexity and cost of the preparing process.

In addition, when the microneedle patch is specially used for delivering active pharmaceutical ingredients or vaccine active ingredients, how to control their carrying quantity becomes quite important. In general, a length of microneedle structure ranges from 100 micrometers ($\mu$m) to 1000 $\mu$m, and a thickness of epidermis is various depending on the skin of different body parts and may range from 30 $\mu$m to 300 $\mu$m. In order to exert the expected effects of the carrying quantity of the active ingredients, the carried active ingredients need to be limited to near the needle tip of the microneedle structure, so as to accurately release the active ingredients to the targeted epidermis. If the carried active ingredients diffuse all over the whole microneedle structure, the expected effects cannot be achieved. In that situation, the carrying quantity of the active ingredients must increase to achieve the expected effects, which wastes the active ingredients. The foresaid method does not give any teaching or hint on how to effectively control the carrying quantity of the active pharmaceutical ingredients or vaccine active ingredients in the microneedle patch, which gives a need to improve the prior art method.

SUMMARY OF THE INVENTION

Based on the above-mentioned drawbacks of the prior arts, the objective of the present invention is to effectively limit the active ingredients to the needle tip of the microneedle patch and accurately control the carrying quantity thereof to provide a microneedle patch applicable to pharmaceutical and vaccine fields.

To achieve the above-mentioned objective, the present invention provides a microneedle patch, which comprises a substrate part and multiple needle parts protruding from the substrate part; the substrate part consists of a diffusion-proof layer and a base, and each needle part consists of a needle tip, a diffusion-proof layer and a base, and the diffusion-proof layer of each needle part is formed between the needle tip and the base of the corresponding needle part; wherein the diffusion-proof layer of the substrate part and the diffusion-proof layer of the needle parts are one-piece structures, and the base of the substrate part and the base of the needle parts are one-piece structures; a thickness of each needle part is 300 $\mu$m to 1000 $\mu$m, and a thickness of the substrate part is 200 $\mu$m to 400 $\mu$m; along a thickness measuring line from the base of the substrate part toward a tip of the needle part, a thickness ratio of a sum of a thickness of the base of the needle part and a thickness of the diffusion-proof layer of the needle part relative to a thickness of the needle part is 0.54 to 0.81; wherein, a material of the needle tip comprises hyaluronic acid (HA), polyvinylpyrrolidone (PVP) and a first carbohydrate, and a molecular weight of HA ranges from 2000 Dalton to 500000 Dalton, and a weight ratio of HA relative to PVP is 1:0.8 to 1:2; a material of the diffusion-proof layer comprises a second carbohydrate, poly(vinyl alcohol) (PVA) and 2-hydroxypropyl-$\beta$-cyclodextrin (HP-$\beta$-CD), and a weight ratio of the second carbohydrate relative to PVA is 1:1.8 to 1:3, and a weight ratio of the second carbohydrate relative to HP-$\beta$-CD is 1:1.8 to 1:3; and a material of the base comprises a third carbohydrate, PVA and HP-$\beta$-CD, and a weight ratio of the third carbohydrate relative to PVA is 1:1.8 to 1:3, and a weight ratio of the third carbohydrate relative to HP-$\beta$-CD is 1:1.8 to 1:3.

By simultaneously controlling the compositions of the needle tip, the diffusion-proof layer and the base, the thickness of the needle part and the substrate part, and the thickness ratio of the sum of the thickness of the base and the diffusion-proof layer of the needle part relative to the thickness of the needle part, the diffusion-proof layer can exert diffusion-proof effect and limit the active ingredients to the needle tip to prevent from diffusing to the base, which contributes to controlling the carrying quantity of the active ingredients and achieving the expected effects.

In accordance with the present invention, said "a thickness measuring line from the base of the substrate part toward a tip of the needle part" indicates that a shortest distance of a projection point of the tip of the needle part on the substrate part extending toward the tip of the needle part is set as the thickness measuring line. Specifically, the substrate part has a bottom plane opposite to the needle part, and a shortest distance of a projection point of the tip of the needle part on the bottom plane extending toward the tip of the needle part is set as the thickness measuring line. It should be understood that said "the thickness of the base of the substrate part", "the thickness of the base of the needle part", "the thickness of the diffusion-layer of the needle part" and "the thickness of the needle tip" in the specification are all obtained by measuring along the thickness measuring line.

In accordance with the present invention, the needle layer further comprises glycerol and polysorbate 20 (Tween-20).

In accordance with the present invention, the first carbohydrate is selected from the group consisting of: glucose, galactose, sucrose, trehalose, maltose, lactose, dextrin, maltodextrin, β-cyclodextrin, HP-β-CD, glucan and any combination thereof.

In accordance with the present invention, the second carbohydrate is selected from the group consisting of: trehalose, amylose, amylopectin, chitin, carboxymethyl cellulose (CMC), sodium carboxymethyl cellulose, methylcellulose (MC), hydroxyethyl cellulose (HEC), hydroxypropyl methylcellulose (HPMC), hydroxypropyl cellulose (HPC), gelatin, chitosan and any combination thereof.

In accordance with the present invention, the third carbohydrate is selected from the group consisting of: trehalose, amylose, amylopectin, chitin, CMC, sodium carboxymethyl cellulose, MC, HEC, HPMC, HPC, gelatin, chitosan and any combination thereof.

In accordance with the present invention, the needle tip further comprises an active ingredient. The active ingredient may be an active pharmaceutical ingredients or a vaccine active ingredient. Specifically, the active pharmaceutical ingredient may be a small molecular compound, a biological product, a biosimilar, a protein drug or a botanical. Specifically, the vaccine active ingredient may be an attenuated vaccine, an inactivated vaccine, a virus-like particle (VLP), a purified subunit antigen, a recombinant antigen, a synthetic peptide, a recombinant vector, a DNA vaccine, a nucleic acid vaccine, a mucosal immunization or a combined vaccine.

In accordance with the present invention, a mechanical strength of the needle part of the microneedle patch is more than 0.058 N/needle, such that the microneedle patch of the present invention is able to pierce the stratum corneum without breakage. Preferably, the mechanical strength of the needle part of the microneedle patch is more than 0.14 N/needle. More preferably, the mechanical strength of the needle part of the microneedle patch is more than 0.20 N/needle.

In accordance with the present invention, a weight ratio of HA relative to the first carbohydrate is 1:5 to 1:8.

In one embodiment, the thickness of the needle part, i.e., the needle length of the needle part, is 400 um to 1000 um. In another embodiment, the thickness of the needle part is 600 um to 900 um.

In one embodiment, the thickness of the needle tip is 170 um to 190 μm. In another embodiment, the thickness of the needle tip is 210 um to 240 μm. In another embodiment, the thickness of the needle tip is 170 um to 265 μm. In another embodiment, the thickness of the needle tip is 200 um to 265 μm.

In one embodiment, a thickness of the diffusion-proof layer of the substrate part is 110 μm to 210 μm. It should be understood that the diffusion-proof layer of the substrate part indicates the diffusion-proof layer outside the area where the needle part is formed from the substrate part.

In one embodiment, the thickness of the substrate part is 200 μm to 360 μm. In another embodiment, the thickness of the substrate part is 210 μm to 360 μm.

In one embodiment, a sum of a thickness of the base of the substrate part, the thickness of the base of the needle part and the thickness of the diffusion-proof layer of the needle part is 550 μm to 1100 In another embodiment, the sum of the thickness of the base of the substrate part, the thickness of the base of the needle part and the thickness of the diffusion-proof layer of the needle part is 570 μm to 1100 μm.

In accordance with the present invention, a method of manufacturing the foresaid microneedle patch comprises the following steps:

step (a): providing a master mold having a datum plane and multiple holes, and the multiple holes formed by recessing from the datum plane;

step (b): filling the multiple holes with a needle tip solution, wherein a solid content of the needle tip solution is more than 5 weight percent (wt %) and less than 40 wt %; the needle tip solution comprises HA, PVP and a first carbohydrate, wherein a molecular weight of HA ranges from 2000 Dalton to 500000 Dalton, and a weight ratio of HA relative to PVP is 1:0.8 to 1:2;

step (c): drying the needle tip solution to form a needle tip, and a surface of the needle tip is lower than the datum plane;

step (d): filling the multiple holes with a diffusion-proof solution, and the diffusion-proof solution covers the needle tip and the datum plane, such that a vertical distance between a surface of the diffusion-proof solution and the datum plane is 600 μm to 1500 μm; a solid content of the diffusion-proof solution is more than 30 wt % and less than or equal to 45 wt %, and the diffusion-proof solution comprises a second carbohydrate, PVA and HP-β-CD, wherein a weight ratio of the second carbohydrate relative to PVA is 1:1.8 to 1:3, and a weight ratio of the second carbohydrate relative to HP-β-CD is 1:1.8 to 1:3;

step (e): drying the diffusion-proof solution to form a diffusion-proof layer, and the diffusion-proof layer is formed on the needle tip and the datum plane;

step (f): filling the multiple holes with a base solution, and the base solution covers the diffusion-proof layer in the multiple holes and the diffusion-proof layer formed on the datum plane, such that a vertical distance between a surface of the base solution and the datum plane is 450 μm to 850 μm; a solid content of the base solution is more than or equal to 30 wt % and less than 45 wt %, and the base solution comprises a third carbohydrate, PVA and HP-β-CD, wherein a weight ratio of the third carbohydrate relative to PVA is 1:1.8 to 1:3, and a weight ratio of the third carbohydrate relative to HP-β-CD is 1:1.8 to 1:3; the solid content of the base solution is less than the solid content of the diffusion-proof solution;

step (g): drying the base solution to form a base, such that the diffusion-proof layer is adhered to and located between the needle tip and the base; and step (h): demolding the needle tip, the diffusion-proof layer and the base that are adhered to each other from the master mold to obtain the microneedle patch.

According to the method of manufacturing microneedle patch, the microneedle patch therefrom can limit the active ingredients to the needle tip to prevent from diffusing to the base, which contributes to accurately controlling the quantity of releasing the active ingredient and prevents waste of the active ingredients.

In accordance with the present invention, the master mold may be hard master mold, and materials of the hard master mold may be glass, quartz, silicon wafer, metal, metal oxide or metal alloy. The said metal may be, but is not limited to, aluminum, copper or nickel. In another embodiment, the master mold may be soft master mold, and materials of the soft master mold may be polymer, metal foil or flexible glass. The said polymer may be, but is not limited to, poly(dimethylsiloxane) (PDMS), poly(methylmethacrylate) (PMMA), polycarbonate (PC) or polyethersulfone (PES).

In accordance with the present invention, the shape of the multiple holes of the master mold may be, but is not limited to, cone-shape, pyramid-shape or steeple-shape. In the master mold, the master mold has a datum plane and multiple holes, and each hole is formed by recessing from the datum plane. The depth of each hole ranges from 75 μm to 1500 μm; preferably, ranges from 150 μm to 1200 μm; more preferably, ranges from 175 μm to 1000 μm; even more preferably, ranges from 200 μm to 1000 μm. The maximum width of each hole ranges from 38 μm to 800 μm; preferably, ranges from 75 μm to 650 μm; more preferably, ranges from 85 μm to 550 μm.

In the said microneedle patch, the needle shape of each needle part may be, but is not limited to, cone-shape, pyramid-shape or steeple-shape.

In the said microneedle patch, the density of the needle parts may range from 1 needle/cm$^2$ to 1000 needles/cm$^2$; preferably, range from 1 needle/cm$^2$ to 500 needles/cm$^2$.

In accordance with the present invention, the needle tip solution further comprises glycerol and polysorbate 20.

In accordance with the present invention, based on a total weight of the needle tip solution, a content of glycerol is 0.005 wt % to 0.2 wt %, and a content of polysorbate 20 is 0.001 wt % to 0.1 wt %.

In accordance with the present invention, a viscosity of the needle tip solution is measured at a shear rate of 1 s$^{-1}$ at 25° C., and the viscosity of the needle tip solution is 8 centipoise (cP) to 25000 cP; preferably, is 8 cP to 20000 cP.

In accordance with the present invention, a viscosity of the diffusion-proof solution is measured at a shear rate of 1 s$^{-1}$ at 25° C., and the viscosity of the diffusion-proof solution is 5000 cP to 220000 cP; preferably, is 10000 cP to 200000 cP; more preferably, is 30000 cP to 200000 cP.

In accordance with the present invention, a viscosity of the base solution is measured at a shear rate of 1 s$^{-1}$ at 25° C., and the viscosity of the base solution is 3000 cP to 100000 cP; preferably, is 5000 cP to 100000 cP; more preferably, is 7000 cP to 90000 cP.

In accordance with the present invention, all of the needle tip solution, the diffusion-proof solution and the base solution may be polymer aqueous solution, and the needle tip solution is polymer aqueous solution containing active ingredients. Preferably, the solid content of the needle tip solution is 10 wt % to 35 wt %.

In accordance with the present invention, the polymer materials contained in the needle tip solution, the diffusion-proof solution and the base solution may be dissolvable or swellable materials. More specifically, the polymer materials may be biocompatible materials or biodegradable materials. For example, the polymer materials may be, but are not limited to, amylopectin, starch, sodium hyaluronate, poly (methyl vinyl ether-alt-maleic anhydride (PMVE/MA), CMC, MC, HPMC, HPC, gelatin, PVA, PVP, polyethylene glycol (PEG), polylactic acid (PLA), poly(glycolic acid) (PGA), poly(lactic-co-glycolic acid) (PLGA), chitosan or any combination thereof. When the polymer materials comprise glucose, galactose, lactose, sucrose, trehalose, maltose, dextrin, maltodextrin, β-cyclodextrin, HIP-β-CD, glucan, the mechanical strength of the microneedle patch can be enhanced. Besides, when applying the microneedle patch in the vaccine field, said glucose, galactose, lactose, sucrose, trehalose, maltose or dextrin, etc. can also be an adjuvant.

Preferably, the step (b) may further comprise:

step (b1): forming the needle tip solution on the master mold, and making the needle tip solution flow into the multiple holes to cover the datum plane and the multiple holes; and step (b2): removing the needle tip solution above the datum plane to align the surface of the needle tip solution to the datum plane.

In accordance with the present invention, the method comprises: filling the multiple holes with the needle tip solution by vacuum evacuation and centrifugation in the step (b). In one embodiment, the needle tip solution and the master mold may be placed in an oven for evacuation to make the needle tip solution cover the datum plane and the multiple holes; in another embodiment, the needle tip solution and the master mold may be centrifuged together to make the needle tip solution cover the datum plane and the multiple holes. Here, a pressure of the oven may be −700 mmHg to −800 mmHg; preferably, −710 mmHg to −760 mmHg, and a rotational speed of the centrifugation may be 20×g to 20000×g; preferably, 20×g to 12000×g.

Preferably, the step (d) may further comprise:

step (d1): forming the diffusion-proof solution on the master mold, and making the diffusion-proof solution flow into the multiple holes to cover the datum plane and the multiple holes; and step (d2): removing a part of the diffusion-proof solution above the datum plane to make the vertical distance between the surface of the diffusion-proof solution and the datum plane be 600 μm to 1500 μm.

In accordance with the present invention, the method comprises: filling the multiple holes with the diffusion-proof solution by vacuum evacuation and centrifugation in the step (d). In one embodiment, the diffusion-proof solution and the master mold may be placed in an oven for evacuation to make the diffusion-proof solution cover the datum plane and the multiple holes; in another embodiment, the diffusion-proof solution and the master mold may be centrifuged together to make the diffusion-proof solution cover the datum plane and the multiple holes. Here, a pressure of the oven may be −700 mmHg to −800 mmHg; preferably, −710 mmHg to −760 mmHg, and a rotational speed of the centrifugation may be 20×g to 20000×g; preferably, 20×g to 12000×g.

Preferably, the step (f) may further comprise:

step (f1): forming the base solution on the master mold, and making the base solution flow into the multiple holes to cover the diffusion-proof layer on the datum plane and the diffusion-proof layer in the multiple holes; and step (f2): removing a part of the base solution above the datum plane to make the vertical distance between the surface of the base solution and the datum plane be 450 μm to 850 μm.

In accordance with the present invention, the method comprises: filling the multiple holes with the base solution by vacuum evacuation and centrifugation in the step (f). In one embodiment, the base solution and the master mold may be placed in an oven for evacuation to make the base solution cover the diffusion-proof layer on the datum plane and the diffusion-proof layer in the multiple holes; in another embodiment, the base solution and the master mold may be centrifuged together to make the base solution cover the diffusion-proof layer on the datum plane and the diffusion-proof layer in the multiple holes. Here, a pressure of the oven may be −700 mmHg to −800 mmHg; preferably, −710 mmHg to −760 mmHg, and a rotational speed of the centrifugation may be 20×g to 20000×g; preferably, 20×g to 12000×g.

Preferably, in the step (b), step (d) and step (f), respectively, the needle tip solution, the diffusion-proof solution and the base solution may be formed on the master mold by, but not limited to, slit or slot die coating, blade coating, slide coating, dip coating, inkjet printing, nozzle printing, dispenser or any combination thereof. The needle tip solution in the step (b), the diffusion-proof solution in the step (d) and the base solution in the step (f) may be formed on the master mold by the same way or different ways. Preferably, in the method of manufacturing the microneedle patch, the needle tip solution, the diffusion-proof solution and the base solution may be sequentially formed on the master mold by slit or slot die coating. More preferably, in the method of manufacturing the microneedle patch, the needle tip solution, the diffusion-proof solution and the base solution may be sequentially formed on the master mold by dispenser.

In one embodiment, when slit or slot die coating is adopted to coat the needle tip solution in the step (b), the coating gap may be 1 μm to 5000 μm, and the coating speed may be 1 meter/minute (m/min) to 100 m/min. The process parameters are adjustable depending on the properties of the needle tip solution and the specification of the microneedle patch. When slit or slot die coating is adopted to coat the diffusion-proof solution in the step (d), the coating gap may be 1 μm to 3000 μm, and the coating speed may be 1 m/min to 100 m/min. Besides, when slit or slot die coating is adopted to coat the base solution in the step (f), the coating gap may be 1 μm to 3000 μm, and the coating speed may be 1 m/min to 100 m/min. The process parameters are adjustable depending on the properties of the diffusion-proof solution and the base solution and the specification of the microneedle patch.

Preferably, in the step (b), the coating gap may be 100 μm to 5000 μm, and the coating speed may be 1 m/min to 100 m/min; in the step (d), the coating gap may be 100 μm to 3000 μm, and the coating speed may be 1 m/min to 100 m/min; and in the step (f), the coating gap may be 100 μm to 3000 μm, and the coating speed may be 1 m/min to 100 m/min.

In the specification, said "wet film thickness" indicates a vertical distance between a surface of a liquid and the datum plane of the master mold after the liquid is placed on the master mold and then covers the multiple holes of the master mold. For example, "a wet film thickness of the diffusion-proof solution is 600 μm to 1500 μm" indicates that the vertical distance of the surface of the diffusion-proof solution and the datum plane of the master mold is 600 μm to 1500 μm after the diffusion-proof solution is filled into the master mold and then covers the needle tip. Preferably, in the step (d), the vertical distance between the surface of the diffusion-proof solution and the datum plane is 600 μm to 850 μm.

In accordance with the present invention, the step (c), the step (e) and the step (g) may be accomplished by freeze drying or drying at room temperature. Preferably, the drying temperature in the step (c), the step (e) and the step (g) may be −80° C. to 100° C. More specifically, when manufacturing the microneedle patch for the pharmaceutical field, the drying temperature in the step (c), the step (e) and the step (g) may be −80° C. to 100° C. in order to prevent inactivation of the active pharmaceutical ingredients due to the destruction of molecular structure caused by the drying temperature over 100° C. On the other hand, when manufacturing the microneedle patch for the vaccine field, the drying temperature in the step (c), the step (e) and the step (g) may be −80° C. to 40° C. in order to prevent inactivation of the vaccine caused by the drying temperature over 40° C.

In the specification, said "a wet film thickness of the base solution is 450 μm to 850 μm" indicates that the vertical distance of the surface of the base solution and the datum plane of the master mold is 450 μm to 850 μm after the base solution is filled into the master mold and then covers the diffusion-proof layer. Preferably, in the step (f), the vertical distance between the surface of the base solution and the datum plane is 450 μm to 750 μm.

In application, by controlling the length of the needle parts, the microneedle patch can prevent reaching the nerve system below the epidermis, thereby reducing the fear and pain in use.

In the specification, a range represented by "a lower-endpoint value to an upper-endpoint value", if not particularly specified, indicates that the range is more than or equal to the lower-endpoint value and less than or equal to the upper-endpoint value. For example, "the thickness is 300 μm to 1000 μm" indicates that the range of thickness is "more than or equal to 300 μm and less than or equal to 1000 μm".

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
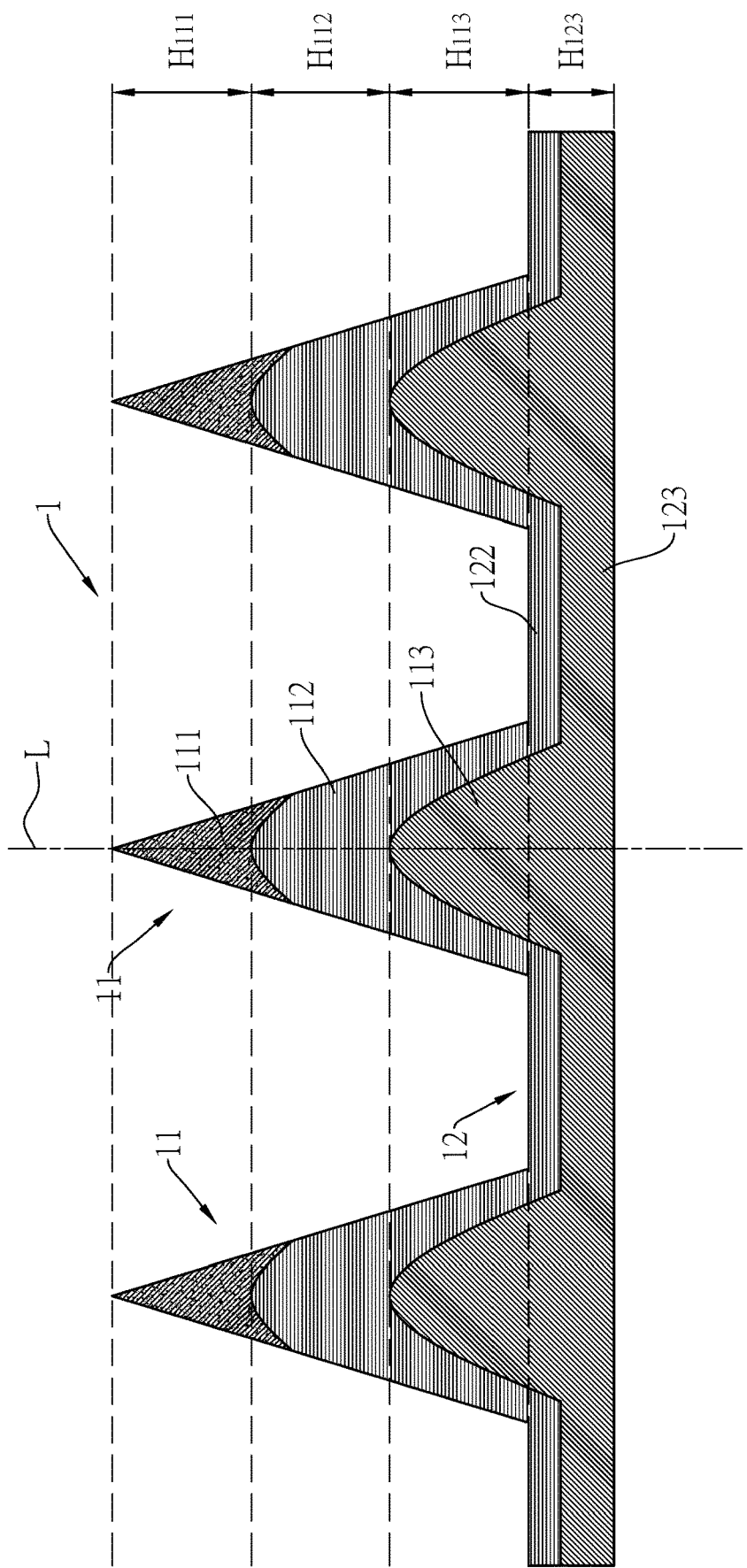
FIG. 1 is a schematic figure for demonstrating that the diffusion-proof layer of the microneedle patches of Examples have the expected diffusion-proof effects.

Several microneedle patches and methods for manufacturing the same are exemplified below to illustrate the implementation of the present invention. One person skilled in the art can easily realize the advantages and effects of the present invention in accordance with the contents disclosed in the specification. Various modifications and variations could be made in order to practice or apply the present invention without departing from the spirit and scope of the invention.

Description of Reagents

1. Hyaluronic acid (HA), molecular weight: 100000 Dalton, purchased from ECHO CHEMICAL CO., LTD.
2. Polyvinylpyrrolidone (PVP), purchased from WEI MING PHARMACEUTICAL MFG. CO., LTD.
3. Sucrose, purchased from ECHO CHEMICAL CO., LTD.
4. Trehalose, purchased from ECHO CHEMICAL CO., LTD.
5. Polyvinyl alcohol (PVA), purchased from YES TOP APPLIED MATERIALS CO., LTD.
6. 2-hydroxypropyl-β-cyclodextrin (HP-β-CD), product name: Cavitron W7 HP7 Pharm, purchased from SHANG KO BIOMED CO., LTD.
7. Glycerol, purchased from ECHO CHEMICAL CO., LTD.
8. Polysorbate 20 (Tween-20), product name: MASEMUL PS 20, purchased from YUE BA ENTERPRISE CO., LTD.

Preparation of Polymer Materials

The present invention prepared three different compositions of polymer materials for preparing the needle tip solution of the needle tip, the diffusion-proof solution of the diffusion-proof layer and the base solution of the base. Table 1 shows the compositions and their weight ratio of the polymer materials marked with A, B and C.

TABLE 1

The compositions and their weight ratio of the polymer materials.

| Mark | The compositions and their weight ratio of the polymer materials |
|---|---|
| A | HA (molecular weight: 100000 Dalton):PVP:sucrose = 2:2:11 |
| B | HA (molecular weight: 100000 Dalton):PVP:trehalose = 2:2:11 |
| C | trehalose:PVA:HP-β-CD = 1:2:2 |

Test Example 1: Viscosity Evaluation

In this test example, suitable amounts of polymer materials A, B and C were dissolved in different solvents to prepare the needle tip solution, the diffusion-proof solution and the base solution with different solid contents, respectively. Meanwhile, glycerol and Tween-20 were additionally added according to Table 2 to obtain test examples. Here, the polymer material A was dissolved in phosphate buffered saline (PBS), and the polymer materials B and C were dissolved in deionized water (DI water). Taking the needle tip solution of Example 1 for example, it comprised 10 wt % of polymer material A, 0.0067 wt % of glycerol, 0.011 wt % of Tween-20 and PBS for the rest. Also, taking the diffusion-proof solution of Example 1 for example, it comprised 40 wt % of polymer material C and 60 wt % of DI water. Again, taking the base solution of Example 1 for example, it comprised 35 wt % of polymer material C and 65 wt % of DI water.

Next, the viscosity of the test examples was measured at a shear rate of 1 s$^{-1}$ at 25° C. by a viscometer (model: MCR302, purchased from Anton Parr), and listed in Table 2.

Examples 1 to 9: Microneedle Patch

As shown in Table 2, the foresaid needle tip solution, diffusion-proof solution and base solution were adopted, and then the microneedle patches of Examples 1 to 9 were prepared respectively by following the method below.

First, a master mold with a datum plane and multiple holes was adopted. The multiple holes were formed by recessing from the datum plane, and arranged in array on the master mold. The material of the master mold was polydimethylsiloxane (PDMS), the density of the multiple holes was 266 holes/cm$^2$, the range of the array-arranged multiple holes was a circle with a diameter of 1.5 cm, and the shape of each hole was the shape of a pyramid. In Examples 1 to 8, the depth of each hole, i.e. the vertical distance between the tip of each hole and the datum plan, was about 580 μm to 620 μm, and the maximum width of each hole, i.e. the maximum inner diameter of the cross-section of each hole that aligned to the datum plane, was about 290 μm to 310 μm. In Example 9, the depth of each hole, i.e. the vertical distance between the tip of each hole and the datum plan, was about 880 μm to 920 μm, and the maximum width of each hole, i.e. the maximum inner diameter of the cross-section of each hole that aligned to the datum plane, was about 440 μm to 460 μm.

Next, 0.1 milliliter (ml) of the needle tip solution was dropped on the master mold and covered the multiple holes thereof by dispenser. Then, the master mold with the needle tip solution was placed into a vacuum oven for evacuation to reduce the pressure to −730 mmHg to −760 mmHg, such that the needle tip solution flowed downward into the multiple holes from the datum plane, and covered the datum plane and all holes. Here, the step could also be conducted by centrifugation; for example, the master mold with the needle tip solution was placed into a centrifuge, and then centrifuged at 2300×g for 6 minutes to make the needle tip solution flow downward into the multiple holes from the datum plane, and covered the datum plane and all holes. Afterwards, the needle tip solution above the datum plane was totally removed by a blade, and the master mold with the needle tip solution was placed into an environment at 30° C. and with the relative humidity (RH) of 20% to 65% for 1 hour to dry the needle tip solution into the needle tip. Here, the thickness of the needle tip (dry film thickness) of the microneedle patches of Examples 1 to 9 indicated the vertical distance between the tip of the hole and the surface of the needle tip, and if the surface of the needle tip was not a flat plane but a concave plane, the thickness of the needle tip (dry film thickness) would be the vertical distance between the tip of the hole and the lowest spot on the concave plane. The ratio of the thickness of the needle tip relative to the depth of the hole of the master mold, i.e., the ratio of the thickness of the needle tip relative to the thickness of the needle part, of the microneedle patches of Examples 1 to 9 were listed in the following Table 3.

Next, 0.8 ml of the diffusion-proof solution was dropped on the master mold formed with the needle tip and covered the multiple holes thereof by dispenser. Then, the master mold with the diffusion-proof solution was placed into a centrifuge, and then centrifuged at 2300×g for 6 minutes to make the diffusion-proof solution flow downward into the multiple holes from the datum plane, and cover the datum plane and the needle tip in all holes. Afterwards, a part of the diffusion-proof solution above the datum plane was removed by a blade to obtain the wet film thickness of the diffusion-proof solution shown in Table 2. For example, the wet film thickness of the diffusion-proof solution being 700 μm indicated that the vertical distance between the datum plane and the surface of the diffusion-proof solution was 700 µm. Then, the master mold with the diffusion-proof solution was placed into an environment at 30° C. and with the RH of 20% to 65% for 24 hours to 48 hours to dry the diffusion-proof solution into the diffusion-proof layer. The diffusion-proof layer was adhered to the needle tip, and the datum plane, and the master mold formed with the needle tip and the diffusion-proof layer was obtained.

Next, 0.8 ml of the base solution was dropped on the master mold formed with the needle tip and the diffusion-proof layer by dispenser, and covered the multiple holes thereof. Then, the master mold with the base solution was placed into a centrifuge, and then centrifuged at 2300×g for 40 minutes to make the base solution flow downward into the multiple holes from the datum plane, and cover the diffusion-proof layer on the datum plane and the diffusion-proof layer in all holes. Afterwards, a part of the base solution above the datum plane was removed by a blade to obtain the wet film thickness of the base solution shown in Table 2. Then, the master mold with the base solution was placed into an environment at 30° C. and with the RH of 20% to 65% for 24 hours to 48 hours to dry the base solution into the base. The base was adhered to the diffusion-proof layer, i.e. the diffusion-proof layer of the needle part was adhered to and located between the needle tip and the base of the needle part, and the master mold with the final product was obtained. Here, when a shortest distance of a projection point of the tip of the hole on the surface of the base extending toward the tip was set as the thickness measuring line, the thickness ratio of the sum of the thickness of the base of the needle part and the thickness of the diffusion-proof layer of the needle part (i.e., the vertical distance between the surface of the needle tip and the datum plane) relative to the thickness of the needle part (i.e., the depth of the hole of the master mold) of the microneedle patches of Examples 1 to 9 were listed in the following Table 3. Besides, the thickness of the substrate part (i.e., the vertical distance between the surface of the base and the datum plane) of the microneedle patches of Examples 1 to 9 were also listed in the following Table 3.

Finally, the final product was demolded from the master mold with the final product to obtain the microneedle patches of Examples 1 to 9. For explanation, in the method of manufacturing the microneedle patch above, the needle tip solution could comprise active pharmaceutical ingredients or vaccine active ingredients.

As shown in FIG. 1, the microneedle patch 1 of the present invention comprised the substrate part 12 and multiple needle parts 11 protruding from the substrate part 12. The substrate part 12 consisted of the diffusion-proof layer of the substrate part 122 and the base of the substrate part 123, and each needle part 11 consisted of the needle tip 111, the diffusion-proof layer of the needle part 112 and the base of the needle part 113, and the diffusion-proof layer of the needle part 112 is formed between the needle tip 111 and the base of the needle part 113. The diffusion-proof layer of the substrate part 122 and the diffusion-proof layer of the needle part 112 are one-piece structures, and the base of the substrate part 123 and the base of the needle part 113 are one-piece structures. The thickness measuring line L was the shortest distance between the projection point of the tip of the needle part on the bottom plane of the substrate part opposite to the needle part and the tip, and the thickness measuring line L was used for measuring the thickness $H_{123}$ of the base of the substrate part 123, the thickness $H_{113}$ of the base of the needle part 113, the thickness $H_{112}$ of the diffusion-proof layer of the needle part 112 and the thickness $H_{111}$ of the needle tip 111. As shown in FIG. 1, when measured along the thickness measuring line L, the thickness $H_{123}$ of the base of the substrate part 123 equaled to the sum of the thickness of the diffusion-proof layer of the substrate part 122 and the base of the substrate part 123, and could be simplified as the thickness of the substrate part 12. When measured along the thickness measuring line L, the sum of the thickness $H_{113}$ of the base of the needle part 113, the thickness $H_{112}$ of the diffusion-proof layer of the needle part 112 and the thickness $H_{111}$ of the needle tip 111 was the thickness of the needle part 11. The ratio of the sum of the thickness $H_{113}$ of the base of the needle part 113 and the thickness $H_{112}$ of the diffusion-proof layer of the needle part 112 relative to the depth of the hole of the master mold (i.e., the thickness of the needle part) of the microneedle patches of Examples 1 to 9 were also listed in the following Table 3. In addition, when measured along the thickness measuring line L, the sum of the thickness $H_{123}$ of the base of the substrate part 123, the thickness $H_{113}$ of the base of the needle part 113 and the thickness $H_{112}$ of the diffusion-proof layer of the needle part 112 was 550 µm to 1100 µm.

Besides, as follows, the preparing processes of the diffusion-proof layer and the base of the microneedle patch and FIG. 3A to FIG. 3C were adopted for specifically explaining the meaning of the wet film thickness.

Figure 3A:
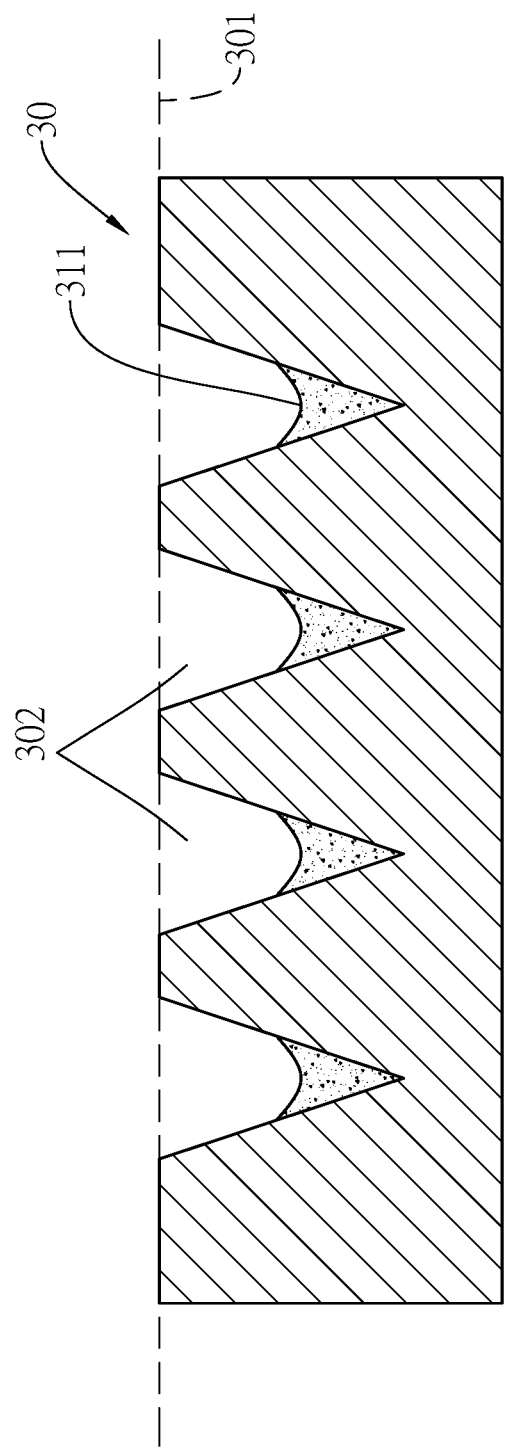
FIG. 3A to FIG. 3C is a schematic figure for explaining the definition of the wet film thickness in the specification.

As shown in FIG. 3A, a master mold 30 with a needle tip had a datum plane 301, multiple holes 302 formed by recessing from the datum plane 301 and a needle tip 311 formed in the multiple holes 301.

Figure 3B:
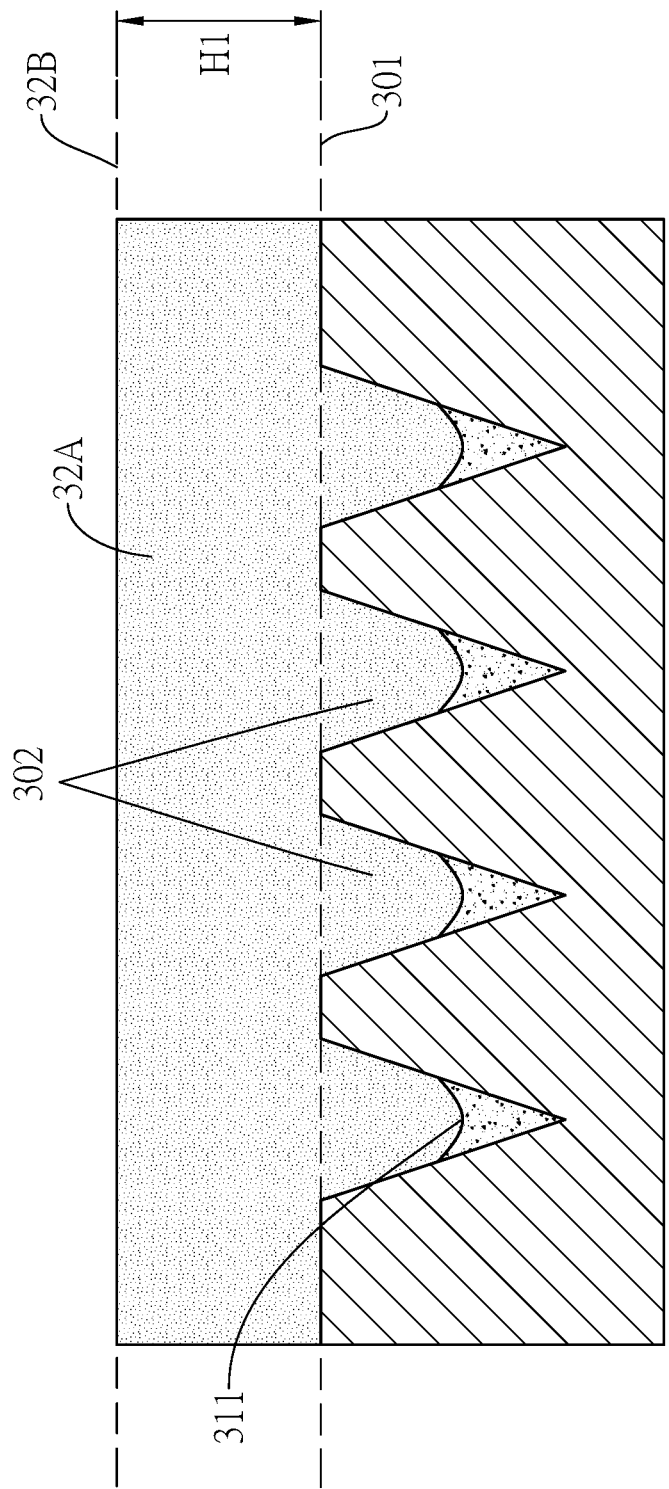

Next, as shown in FIG. 3B, a diffusion-proof solution 32A was filled into the multiple holes 302 and covered the surface of the needle tip 311 and the datum plane 301. Here, a vertical distance H1 between the surface 32B of the diffusion-proof solution 32A and the datum plane 301 was the wet film thickness of the diffusion-proof solution 32A.

Figure 3C:
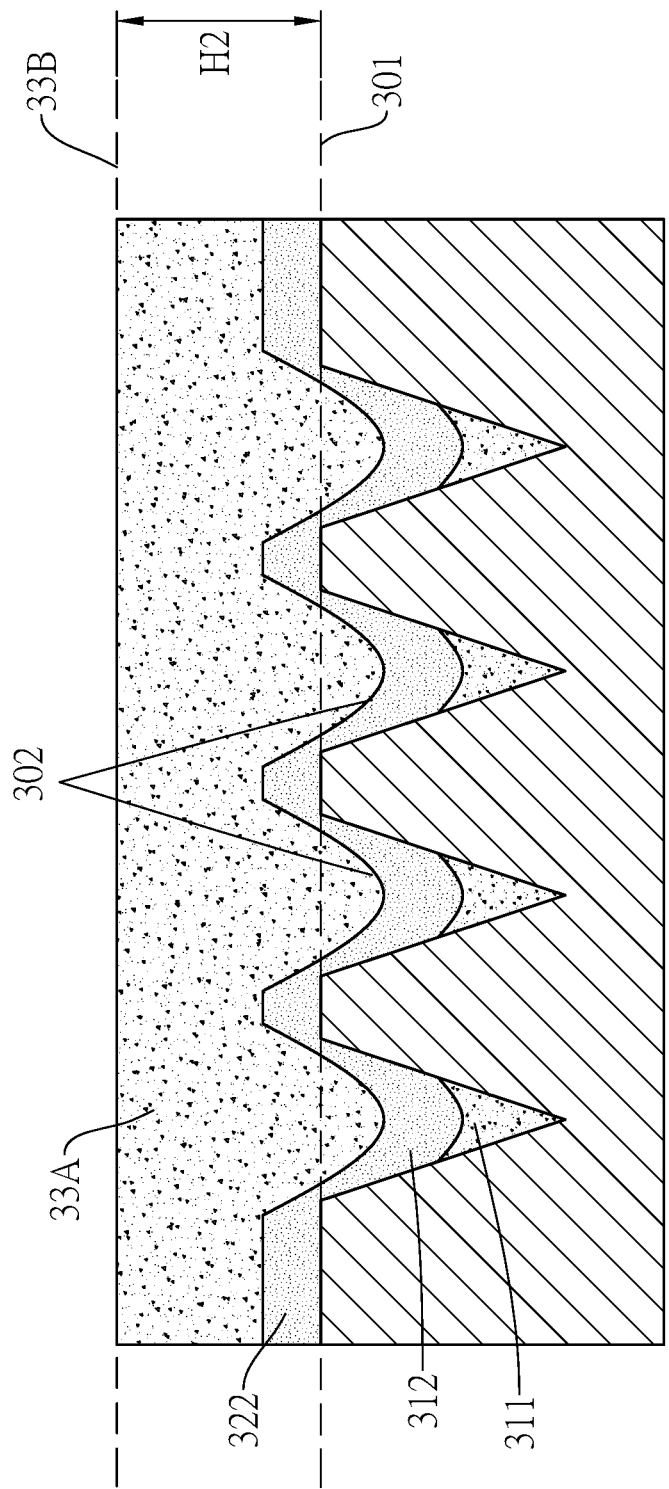

Next, as shown in FIG. 3C, the diffusion-proof solution 32A would form a diffusion-proof layer of the needle part 312 on the surface of the needle tip 311 and a diffusion-proof layer of the substrate part 322 on the datum plane 301. Afterwards, a base solution 33A was filled into the multiple holes 302 and covered the surface of the diffusion-proof layer of the needle part 312 and the surface of the diffusion-proof layer of the substrate part 322. Here, a vertical distance H2 between the surface 33B of the base solution 33A and the datum plane 301 was the wet film thickness of the base solution 33A.

Comparative Examples 1 and 2: Microneedle Patch

The methods of manufacturing the microneedle patches of Comparative Examples 1 and 2 were similar to that of Example 8. The main difference was that the wet film thickness of the base solution of the microneedle patches of Comparative Examples 1 and 2 were different from that of Example 8.

TABLE 2

The compositions and viscosity of the needle tip solution, the compositions, viscosity and wet film thickness of the diffusion-proof solution, and the compositions, viscosity and wet film thickness of the base solution adopted for preparing the microneedle patches of Examples 1 to 9 (E1 to E9) and Comparative Examples 1 and 2 (CE1 and CE2).

| | The needle tip solution | | | | The diffusion-proof solution | | | | The base solution | | | |
|---|---|---|---|---|---|---|---|---|---|---|---|---|
| No. | Polymer material | Solid content (wt %) | Additives (wt %) | Viscosity (cP) | Polymer material | Solid content (wt %) | Viscosity (cP) | Wet film thickness (μm) | Polymer material | Solid content (wt %) | Viscosity (cP) | Wet film thickness (μm) |
| E1 | A | 10 | glycerol (0.0067) Tween-20 (0.011) | 15-65 | C | 40 | 106250-143750 | 600-700 | C | 35 | 30000-44000 | 640-720 |
| E2 | A | 15 | glycerol (0.01) Tween-20 (0.0165) | 130-160 | C | 40 | 106250-143750 | 600-700 | C | 35 | 30000-44000 | 640-720 |
| E3 | A | 20 | glycerol (0.013) Tween-20 (0.022) | 420-480 | C | 40 | 106250-143750 | 600-700 | C | 35 | 30000-44000 | 640-720 |
| E4 | A | 25 | glycerol (0.0167) Tween-20 (0.0275) | 1480-1550 | C | 40 | 106250-143750 | 600-700 | C | 35 | 30000-44000 | 640-720 |
| E5 | A | 30 | glycerol (0.02) Tween-20 (0.03) | 4750-5000 | C | 40 | 106250-143750 | 600-700 | C | 35 | 30000-44000 | 640-720 |
| E6 | A | 35 | glycerol (0.023) Tween-20 (0.0385) | 8405-11300 | C | 40 | 106250-143750 | 600-700 | C | 35 | 30000-44000 | 640-720 |
| E7 | B | 15 | glycerol (0.01) Tween-20 (0.016) | 130-160 | C | 40 | 106250-143750 | 600-700 | C | 35 | 30000-44000 | 640-720 |
| E8 | A | 20 | glycerol (0.013) Tween-20 (0.022) | 420-480 | C | 40 | 106250-143750 | 600-700 | C | 35 | 30000-44000 | 480-520 |
| E9 | A | 16.5 | glycerol (0.011) Tween-20 (0.0182) | 170-230 | C | 40 | 106250-143750 | 600-700 | C | 35 | 30000-44000 | 640-720 |
| CE1 | A | 20 | glycerol (0.013) Tween-20 (0.022) | 420-480 | C | 40 | 106250-143750 | 600-700 | C | 35 | 30000-44000 | 980-1020 |
| CE2 | A | 20 | glycerol (0.013) Tween-20 (0.022) | 420-480 | C | 40 | 106250-143750 | 600-700 | C | 35 | 30000-44000 | 1170-1230 |

TABLE 3

The polymer materials of the needle tip, the diffusion-proof layer and the base,
the ratio of the thickness of the needle tip relative to the thickness of the needle part,
the thickness of the substrate part, the ratio of the sum of the
thickness of the diffusion-proof layer and the base of the needle part relative to the thickness
of the needle part when measured along the thickness measuring line, the mechanical strength,
and the result of diffusion evaluation of the microneedle patches of Examples 1 to 9 (E1 to E9)
and Comparative Examples 1 and 2 (CE1 and CE2).

| No. | Polymer material of the needle tip | The ratio of the thickness of the needle tip relative to the thickness of the needle part | Polymer material of the diffusion-proof layer | Polymer material of the base | The thickness of the substrate part(μm) | The ratio of the sum of the thickness of the diffusion-proof layer and the base of the needle part relative to the thickness of the needle part when measured along the thickness measuring line | Mechanical strength (N/needle) | Diffusion-proof Effect |
|---|---|---|---|---|---|---|---|---|
| E1 | A | 0.275-0.298 | C | C | 260-360 | 0.702-0.725 | 0.14 | ○ |
| E2 | A | 0.282-0.315 | C | C | 260-360 | 0.685-0.718 | 0.23 | ○ |
| E3 | A | 0.353-0.393 | C | C | 260-360 | 0.607-0.647 | 0.29 | ○ |
| E4 | A | 0.368-0.398 | C | C | 260-360 | 0.602-0.632 | 0.29 | ○ |
| E5 | A | 0.402-0.428 | C | C | 260-360 | 0.572-0.598 | 0.27 | ○ |
| E6 | A | 0.420-0.457 | C | C | 260-360 | 0.543-0.580 | 0.22 | ○ |
| E7 | B | 0.325-0.348 | C | C | 260-360 | 0.652-0.675 | 0.22 | ○ |
| E8 | A | 0.353-0.393 | C | C | 210-330 | 0.607-0.647 | 0.22 | ○ |
| E9 | A | 0.207-0.258 | C | C | 220-350 | 0.742-0.793 | 0.3 | ○ |
| CE1 | A | 0.353-0.393 | C | C | 445-462 | 0.607-0.647 | 0.16 | × |
| CE2 | A | 0.353-0.393 | C | C | 506-550 | 0.607-0.647 | 0.05 | × |

Test Example 2: Mechanical Strength Evaluation

The microneedle patches of Examples 1 to 9 and Comparative Examples 1 and 2 were placed in a moisture-proof box for 2 days, and then the mechanical strength of each microneedle patch was measured by a universal testing machine (model: 3343, purchased from INSTRON). In this test example, a compressive test with the displacement set to 10 millimeters (mm) and the speed set to 66 mm/min was conducted, and 500 compressive stress values were received per second at the same time. The mechanical strength of the microneedle patches of Examples 1 to 9 and Comparative Examples 1 and 2 were listed in Table 3.

According to the results in Table 3, the mechanical strength of the microneedle patches of Examples 1 to 9 were all higher than 0.058 N/needle, and thus could pierce the stratum corneum without breakage. Moreover, the mechanical strength of the microneedle patches of Examples 2 to 9 was all higher than 0.2 N/needle, and the microneedle patches of Example 9 had the best mechanical strength as 0.3 N/needle. In contrast, the mechanical strength of the microneedle patch of Comparative Example 2 was only 0.05 N/needle, and was apparently hard to pierce the stratum corneum and prone to breakage, thereby affecting the use of the microneedle patch.

Test Example 3: Diffusion-Proof Evaluation

Figure 2:
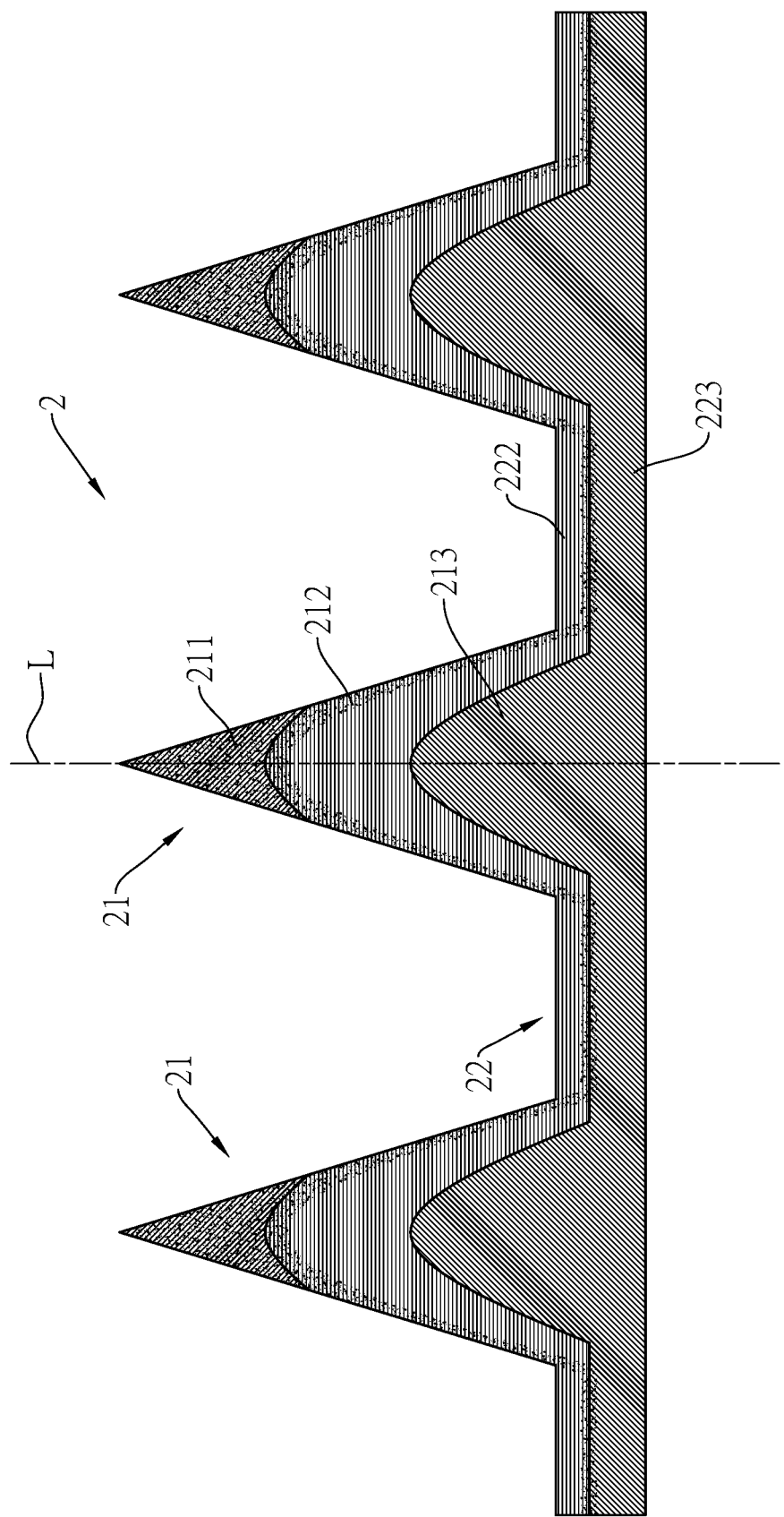
FIG. 2 is a schematic figure for demonstrating that the diffusion-proof layer of the microneedle patches of Comparative Examples do not have the expected diffusion-proof effects.

In this test example, a method of observing the fluorescence with double color was adopted to evaluate whether the diffusion-proof layer can effectively prevent the active ingredients in the needle tip from diffusing to the base, and thus control the carrying quantity of the active ingredients in the needle tip of the microneedle patch. During the preparing processes of the microneedle patches of Examples 1 to 9 and Comparative Examples 1 and 2, green fluorescent was added into the needle tip solution with concentration of 29.6 micrograms/milliliter (μg/ml), and red fluorescent was added into the base solution with concentration of 29.6 μg/ml. After the microneedle patches of Examples 1 to 9 and Comparative Examples 1 and 2 were obtained, each microneedle patch was placed into an inverted fluorescence optical microscope (model: NIB410-FL, purchased from NEXCOPE) to observe whether the diffusion occurred between the layers. If the base still showed red fluorescent by observing with the inverted fluorescence optical microscope, it meant that the green fluorescent in the needle tip did not diffuse. As the needle part 11 of the microneedle patch 1 shown in FIG. 1, the diffusion-proof layer of the needle part 112 thereof had diffusion-proof effect for limiting the active ingredients to the needle tip 111, and such result was marked as "○" in Table 3. On the other hand, if the base showed orange fluorescent, it meant that the green fluorescent in the needle tip diffused to the base and mixed with the red fluorescent in the base. As the needle part 21 of the microneedle patch 2 shown in FIG. 2, the diffusion-proof layer of the needle part 212 thereof did not have diffusion-proof effect, and thus the active ingredients diffused from the needle tip 211 to the base of the substrate part 223, and such result was marked as "×" in Table 3.

According to the results in Table 3, all of the microneedle patches of Examples 1 to 9 could effectively prevent the active ingredients from diffusing from the needle tip to the base. In contrast, both of the microneedle patches of Comparative Examples 1 and 2 could not effectively prevent the active ingredients from diffusing from the needle tip to the base. Especially, although the microneedle patch of Comparative Example 1 had the mechanical strength able to pierce the stratum corneum, it still could not prevent the active ingredients from diffusing from the needle tip to the base, thereby affecting the effects of the microneedle patch with the active ingredients.

In conclusion, by controlling the compositions and thickness of the needle tip, the diffusion-proof layer and the base, the prepared microneedle patch of the present invention not only has good mechanical strength beneficial to use, but also effectively prevent the active ingredients from diffusing from the needle tip to the base for limiting the carried active ingredients to the needle tip, thereby accurately releasing the active ingredients to the target position and ensuring achieving the expected effects.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A microneedle patch, comprising a substrate part and multiple needle parts protruding from the substrate part; the substrate part consisting of a diffusion-proof layer and a base; each needle part consisting of a needle tip, a diffusion-proof layer and a base, and the diffusion-proof layer of each needle part formed between the needle tip and the base of the corresponding needle part; wherein the diffusion-proof layer of the substrate part and the diffusion-proof layer of the needle parts are one-piece structures, and the base of the substrate part and the base of the needle parts are one-piece structures; a thickness of each needle part is 300 μm to 1000 μm, and a thickness of the substrate part is 200 μm to 400 μm; along a thickness measuring line from the base of the substrate part toward the needle tip of the needle part, a thickness ratio of a sum of a thickness of the base of the needle part and a thickness of the diffusion-proof layer of the needle part relative to a thickness of the needle part is 0.54 to 0.81;

wherein, a material of the needle tip comprises hyaluronic acid, polyvinylpyrrolidone and a first carbohydrate, wherein a molecular weight of hyaluronic acid ranges from 2000 Dalton to 500000 Dalton, and a weight ratio of hyaluronic acid relative to polyvinylpyrrolidone is 1:0.8 to 1:2; a material of the diffusion-proof layer comprises a second carbohydrate, poly(vinyl alcohol) and 2-hydroxypropyl-β-cyclodextrin, wherein a weight ratio of the second carbohydrate relative to poly(vinyl alcohol) is 1:1.8 to 1:3, and a weight ratio of the second carbohydrate relative to 2-hydroxypropyl-β-cyclodextrin is 1:1.8 to 1:3; and a material of the base comprises a third carbohydrate, poly(vinyl alcohol) and 2-hydroxypropyl-β-cyclodextrin, wherein a weight ratio of the third carbohydrate relative to poly(vinyl alcohol) is 1:1.8 to 1:3, and a weight ratio of the third carbohydrate relative to 2-hydroxypropyl-β-cyclodextrin is 1:1.8 to 1:3.

2. The microneedle patch as claimed in claim 1, wherein the needle tip further comprises glycerol and polysorbate 20.

3. The microneedle patch as claimed in claim 2, wherein the first carbohydrate is selected from the group consisting of: glucose, galactose, sucrose, trehalose, maltose, lactose, dextrin, maltodextrin, β-cyclodextrin, 2-hydroxypropyl-β-cyclodextrin, glucan and any combination thereof; the second carbohydrate is selected from the group consisting of: trehalose, amylose, amylopectin, chitin, carboxymethyl cellulose, sodium carboxymethyl cellulose, methylcellulose, hydroxyethyl cellulose, hydroxypropyl methylcellulose, hydroxypropyl cellulose, gelatin, chitosan and any combination thereof; the third carbohydrate is selected from the group consisting of: trehalose, amylose, amylopectin, chitin, carboxymethyl cellulose, sodium carboxymethyl cellulose, methylcellulose, hydroxyethyl cellulose, hydroxypropyl methylcellulose, hydroxypropyl cellulose, gelatin, chitosan and any combination thereof.

4. The microneedle patch as claimed in claim 1, wherein the first carbohydrate is selected from the group consisting of: glucose, galactose, sucrose, trehalose, maltose, lactose, dextrin, maltodextrin, β-cyclodextrin, 2-hydroxypropyl-β-cyclodextrin, glucan and any combination thereof; the second carbohydrate is selected from the group consisting of: trehalose, amylose, amylopectin, chitin, carboxymethyl cellulose, sodium carboxymethyl cellulose, methylcellulose, hydroxyethyl cellulose, hydroxypropyl methylcellulose, hydroxypropyl cellulose, gelatin, chitosan and any combination thereof; the third carbohydrate is selected from the group consisting of: trehalose, amylose, amylopectin, chitin, carboxymethyl cellulose, sodium carboxymethyl cellulose, methylcellulose, hydroxyethyl cellulose, hydroxypropyl methylcellulose, hydroxypropyl cellulose, gelatin, chitosan and any combination thereof.

5. The microneedle patch as claimed in claim 4, wherein the needle tip comprises an active ingredient, and the active ingredient comprises an attenuated vaccine, an inactivated vaccine, a virus-like particle, a purified subunit antigen, a recombinant antigen, a synthetic peptide, a recombinant vector, a DNA vaccine, a nucleic acid vaccine, a mucosal immunization or a combined vaccine.

6. The microneedle patch as claimed in claim 1, wherein a weight ratio of hyaluronic acid relative to the first carbohydrate is 1:5 to 1:8.

7. A method of manufacturing the microneedle patch as claimed in claim 1, comprising the following steps:

step (a): providing a master mold having a datum plane and multiple holes, and the multiple holes formed by recessing from the datum plane;

step (b): filling the multiple holes with a needle tip solution, wherein a solid content of the needle tip solution is more than 5 wt % and less than 40 wt %; the needle tip solution comprises hyaluronic acid, polyvinylpyrrolidone and a first carbohydrate, wherein a molecular weight of hyaluronic acid ranges from 2000 Dalton to 500000 Dalton, and a weight ratio of hyaluronic acid relative to polyvinylpyrrolidone is 1:0.8 to 1:2;

step (c): drying the needle tip solution to form a needle tip, wherein a surface of the needle tip is lower than the datum plane;

step (d): filling the multiple holes with a diffusion-proof solution, and the diffusion-proof solution covers the needle tip and the datum plane, such that a vertical distance between a surface of the diffusion-proof solution and the datum plane is 600 μm to 1500 μm; a solid content of the diffusion-proof solution is more than 30 wt % and less than or equal to 45 wt %, and the diffusion-proof solution comprises a second carbohydrate, poly(vinyl alcohol) and 2-hydroxypropyl-β-cyclodextrin, wherein a weight ratio of the second carbohydrate relative to poly(vinyl alcohol) is 1:1.8 to 1:3, and a weight ratio of the second carbohydrate relative to 2-hydroxypropyl-β-cyclodextrin is 1:1.8 to 1:3;

step (e): drying the diffusion-proof solution to form a diffusion-proof layer, wherein the diffusion-proof layer is formed on the needle tip and the datum plane;

step (f): filling the multiple holes with a base solution, wherein the base solution covers the diffusion-proof layer in the multiple holes and the diffusion-proof layer on the datum plane, such that a vertical distance between a surface of the base solution and the datum plane is 450 μm to 850 μm; a solid content of the base solution is more than or equal to 30 wt % and less than 45 wt %, and the base solution comprises a third carbohydrate, poly(vinyl alcohol) and 2-hydroxypropyl-β-cyclodextrin, wherein a weight ratio of the third carbohydrate relative to poly(vinyl alcohol) is 1:1.8 to 1:3, and a weight ratio of the third carbohydrate relative to 2-hydroxypropyl-β-cyclodextrin is 1:1.8 to 1:3; the solid content of the base solution is less than the solid content of the diffusion-proof solution;

step (g): drying the base solution to form a base, such that the diffusion-proof layer is adhered to and located between the needle tip and the base; and step (h): demolding the needle tip, the diffusion-proof layer and the base that are adhered to each other from the master mold to obtain the microneedle patch.

8. The method of manufacturing the microneedle patch as claimed in claim 7, wherein the needle tip solution further comprises glycerol and polysorbate 20.

9. The method of manufacturing the microneedle patch as claimed in claim 8, wherein based on a total weight of the needle tip solution, a content of glycerol is 0.005 wt % to 0.2 wt %, and a content of polysorbate 20 is 0.001 wt % to 0.1 wt %.

10. The method of manufacturing the microneedle patch as claimed in claim 8, wherein a viscosity of the needle tip solution is 8 centipoises to 25000 centipoises.

11. The method of manufacturing the microneedle patch as claimed in claim 8, wherein a viscosity of the diffusion-proof solution is 5000 centipoises to 220000 centipoises.

12. The method of manufacturing the microneedle patch as claimed in claim 8, wherein a viscosity of the base solution is 3000 centipoises to 100000 centipoises.

13. The method of manufacturing the microneedle patch as claimed in claim 8, wherein the first carbohydrate is selected from the group consisting of: glucose, galactose, sucrose, trehalose, maltose, lactose, dextrin, maltodextrin, β-cyclodextrin, 2-hydroxypropyl-β-cyclodextrin, glucan and any combination thereof; the second carbohydrate is selected from the group consisting of: trehalose, amylose, amylopectin, chitin, carboxymethyl cellulose, sodium carboxymethyl cellulose, methylcellulose, hydroxyethyl cellulose, hydroxypropyl methylcellulose, hydroxypropyl cellulose, gelatin, chitosan and any combination thereof; the third carbohydrate is selected from the group consisting of: trehalose, amylose, amylopectin, chitin, carboxymethyl cellulose, sodium carboxymethyl cellulose, methylcellulose, hydroxyethyl cellulose, hydroxypropyl methylcellulose, hydroxypropyl cellulose, gelatin, chitosan and any combination thereof.

14. The method for manufacturing the microneedle patch as claimed in claim 7, wherein in the step (b), a weight ratio of hyaluronic acid relative to the first carbohydrate is 1:5 to 1:8.

15. The method of manufacturing the microneedle patch as claimed in claim 7, wherein in the step (d), the vertical distance between the surface of the diffusion-proof solution and the datum plane is 600 μm to 850 μm.

16. The method of manufacturing the microneedle patch as claimed in claim 7, wherein the first carbohydrate is selected from the group consisting of: glucose, galactose, sucrose, trehalose, maltose, lactose, dextrin, maltodextrin, β-cyclodextrin, 2-hydroxypropyl-β-cyclodextrin, glucan and any combination thereof; the second carbohydrate is selected from the group consisting of: trehalose, amylose, amylopectin, chitin, carboxymethyl cellulose, sodium carboxymethyl cellulose, methylcellulose, hydroxyethyl cellulose, hydroxypropyl methylcellulose, hydroxypropyl cellulose, gelatin, chitosan and any combination thereof; the third carbohydrate is selected from the group consisting of: trehalose, amylose, amylopectin, chitin, carboxymethyl cellulose, sodium carboxymethyl cellulose, methylcellulose, hydroxyethyl cellulose, hydroxypropyl methylcellulose, hydroxypropyl cellulose, gelatin, chitosan and any combination thereof.

17. The method of manufacturing the microneedle patch as claimed in claim 7, wherein the method comprises: filling the multiple holes with the needle tip solution by vacuum evacuation and centrifugation in the step (b); filling the multiple holes with the diffusion-proof solution by vacuum evacuation and centrifugation in the step (d); and filling the multiple holes with the base solution by vacuum evacuation and centrifugation in the step (f).

18. The method of manufacturing the microneedle patch as claimed in claim 7, wherein the needle tip solution comprises an active ingredient, and the active ingredient comprises an attenuated vaccine, an inactivated vaccine, a virus-like particle, a purified subunit antigen, a recombinant antigen, a synthetic peptide, a recombinant vector, a DNA vaccine, a nucleic acid vaccine, a mucosal immunization or a combined vaccine.

* * * * *